(12) United States Patent
Eriksson

(10) Patent No.: US 11,291,856 B2
(45) Date of Patent: Apr. 5, 2022

(54) METHOD, A COMPUTER PROGRAM PRODUCT AND A COMPUTER SYSTEM FOR RADIOTHERAPY

(71) Applicant: RaySearch Laboratories AB, Stockholm (SE)

(72) Inventor: Kjell Eriksson, Bålsta (SE)

(73) Assignee: RaySearch Laboratories AB, Stockholm (SE)

( * ) Notice: Subject to any disclaimer, the term of this patent is extended or adjusted under 35 U.S.C. 154(b) by 255 days.

(21) Appl. No.: 15/580,472

(22) PCT Filed: Jun. 10, 2016

(86) PCT No.: PCT/EP2016/063255
§ 371 (c)(1),
(2) Date: Dec. 7, 2017

(87) PCT Pub. No.: WO2016/198573
PCT Pub. Date: Dec. 15, 2016

(65) Prior Publication Data
US 2019/0111280 A1    Apr. 18, 2019

(30) Foreign Application Priority Data

Jun. 12, 2015  (EP) ..................................... 15171867

(51) Int. Cl.
*A61N 5/10* (2006.01)
*G16H 20/40* (2018.01)
*G16H 50/30* (2018.01)

(52) U.S. Cl.
CPC ......... *A61N 5/1031* (2013.01); *A61N 5/1036* (2013.01); *A61N 5/1045* (2013.01); *G16H 20/40* (2018.01); *G16H 50/30* (2018.01)

(58) Field of Classification Search
CPC ........ A61N 5/103; A61N 5/10; A61N 5/1001; A61N 5/1031; A61N 5/1036;
(Continued)

(56) References Cited

U.S. PATENT DOCUMENTS 8,961,382 B2    2/2015 Nord et al.
2004/0066892 A1*   4/2004 Alber ................... A61N 5/1031
                                                                    378/65

(Continued)

FOREIGN PATENT DOCUMENTS

WO    WO-2014/181204 A2    11/2014

*Primary Examiner* — David P Porta
*Assistant Examiner* — Mamadou Faye
(74) *Attorney, Agent, or Firm* — Faegre Drinker Biddle & Reath LLP

(57) ABSTRACT

A method of optimizing a radiotherapy treatment plan is disclosed, comprising the steps of: a. obtaining a deliverable input treatment plan; b. optimizing the deliverable input treatment plan to obtain an optimized treatment plan, using an objective function and at least one constraint, wherein i. the objective function is related to reducing the plan complexity in terms of minimizing the machine output (MU) and/or minimizing the time required to deliver the plan and/or maximizing the segment area, and/or minimizing jaggedness of the MLC shapes, ii. to ensure that the quality is maintained, the at least one constraint is based on the dose distribution of the input plan, related to maintaining an acceptable dose distribution.

14 Claims, 3 Drawing Sheets

(58) Field of Classification Search
CPC .. A61N 5/1037; A61N 5/1038; A61N 5/1042; A61N 5/1043; A61N 5/1044; A61N 5/1045; A61N 5/1065; A61N 5/107; A61N 5/1048; A61N 5/1077; A61N 2005/1019
See application file for complete search history.

(56) References Cited

U.S. PATENT DOCUMENTS

| | | | |
|---|---|---|---|
| 2006/0067469 A1* | 3/2006 | Dooley | A61N 5/1031 378/65 |
| 2007/0081629 A1* | 4/2007 | Yin | A61N 5/1031 378/65 |
| 2007/0228305 A1* | 10/2007 | Keppel | A61N 5/1031 250/505.1 |
| 2010/0104068 A1 | 4/2010 | Kilby et al. | |
| 2011/0006215 A1* | 1/2011 | Van Heteren | A61N 5/1031 250/453.11 |
| 2012/0020460 A1* | 1/2012 | Witten | A61P 35/00 378/65 |
| 2013/0187062 A1 | 7/2013 | Nord et al. | |
| 2014/0275696 A1* | 9/2014 | Dempsey | A61N 5/1045 600/1 |
| 2015/0095044 A1* | 4/2015 | Hartman | G16H 50/20 705/2 |
| 2015/0367144 A1* | 12/2015 | Flynn | A61N 5/1039 600/7 |
| 2017/0361127 A1* | 12/2017 | Ranganathan | A61N 5/1031 |

* cited by examiner

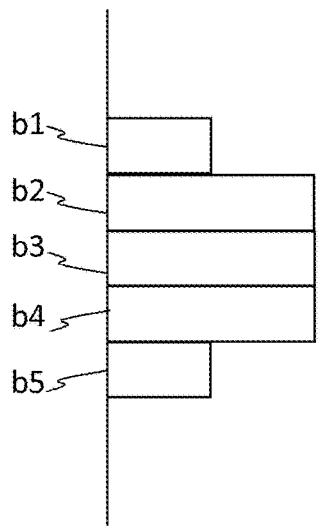 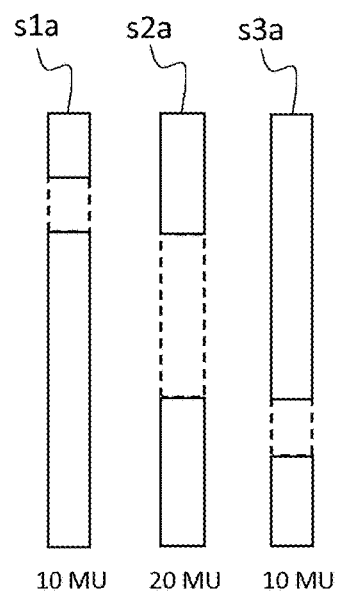 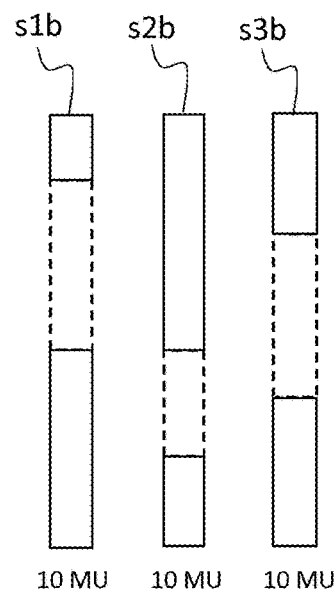
Fig. 1a  Fig. 1b  Fig. 1c
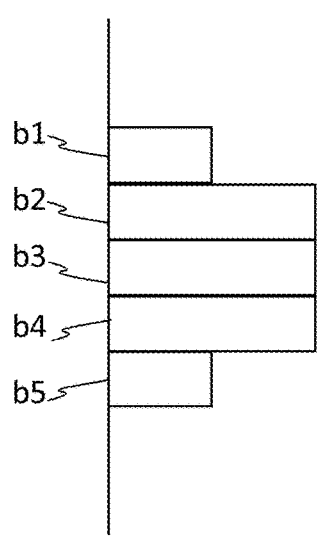 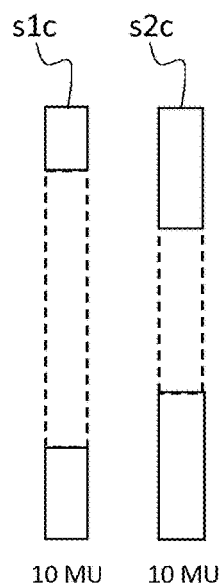
Fig. 2a  Fig. 2b

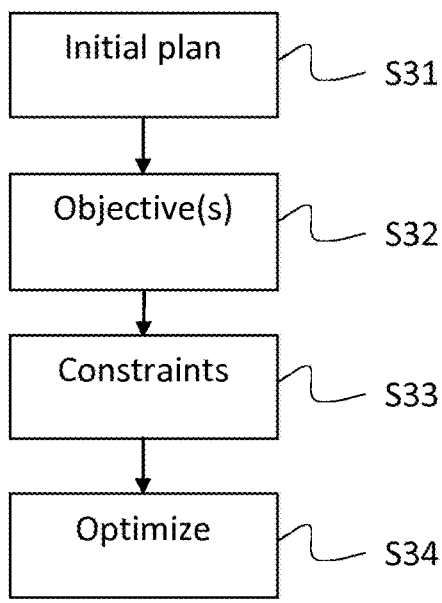
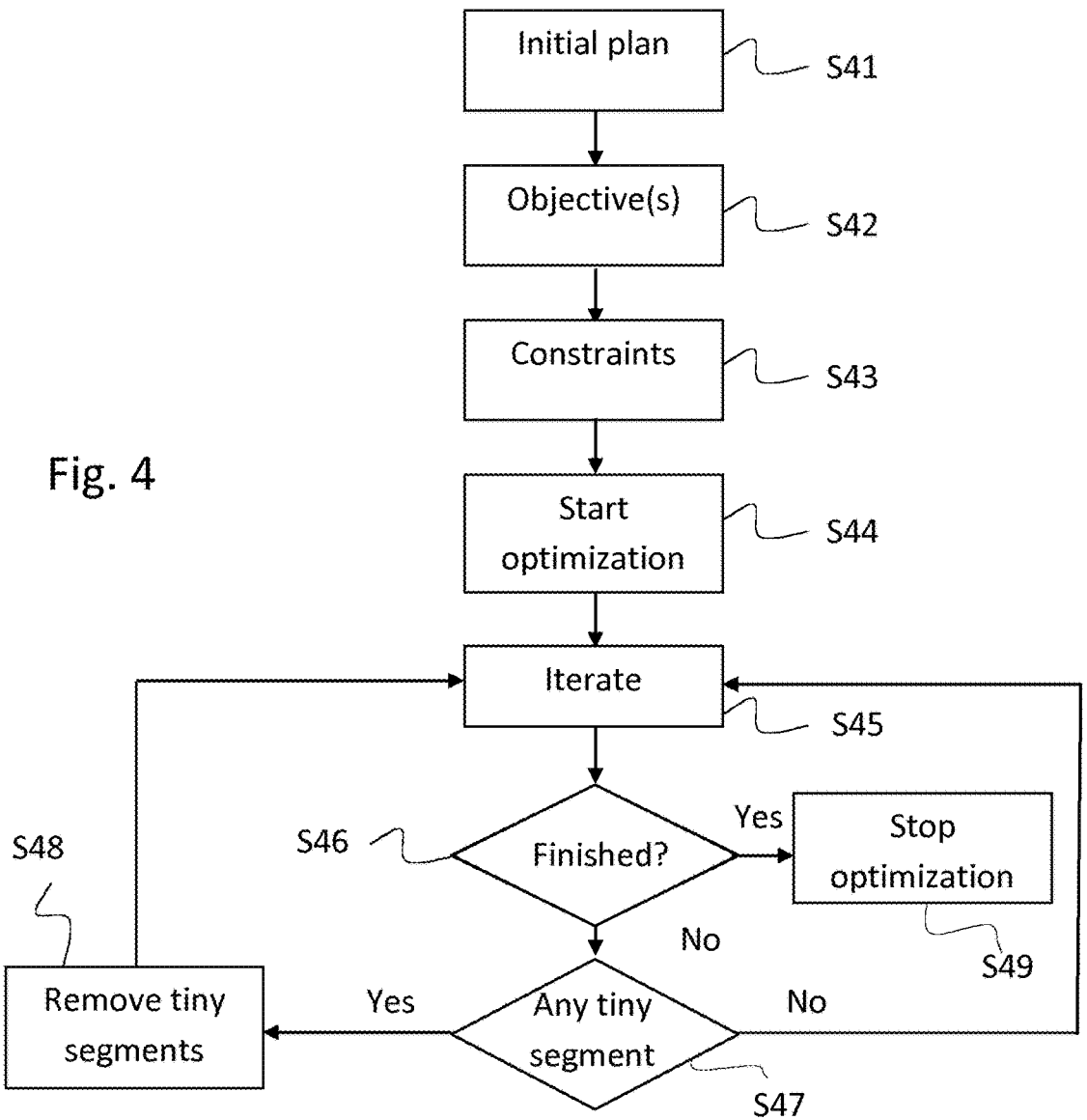
Fig. 3
Fig. 4

METHOD, A COMPUTER PROGRAM PRODUCT AND A COMPUTER SYSTEM FOR RADIOTHERAPY

This application is the National Stage of International Application No. PCT/EP2016/063255, filed Jun. 10, 2016, and claims benefit of European Patent Application No. 15171867.3, filed Jun. 12, 2015, the entire contents of which are incorporated by reference herein.

TECHNICAL FIELD

The present invention relates to the optimization of radiotherapy treatment plans.

BACKGROUND AND RELATED ART

When optimizing radiotherapy treatment plans a number of factors must be taken into account. The most important ones are the objectives that shape the dose distribution, typically including a minimum dose for the target and maximum doses for nearby organs, and in direct machine parameter optimization (DMPO) the machine constraints. Therefore, when developing a treatment plan, typically such minimum and maximum doses for various part of the patient are set and a deliverable treatment plan that fulfils the dose objective as closely as possible is determined. The deliverable treatment plan specifies the beam settings, including beam directions, machine output and the leaf positions of the multileaf collimator (MLC), for the equipment, that will deliver the plan to the patient. The total machine output is expressed in monitor units (MU), whereas the machine output for each beam or segment may be expressed as MU or as a beam or segment weight, respectively. A dose distribution is calculated to verify that the plan quality is within the clinical goals.

In a multi-leaf collimator system this involves setting the opening of the multi-leaf collimator (MLC). A multi-leaf collimator comprises a number of leaves, or pairs of leaves, which may be individually set to define the opening in which the radiation is let through. For step & shoot (SMLC) treatments, radiation is delivered to the patient in a number of beams from different directions. For each beam, a number of segments are defined, which together shape the total dose from a particular direction. Each segment defines the leaf positions to be used for the segment, and the amount of radiation to be delivered to the patient during the segment.

A control point describes which parameters of the treatment machine change during the delivery of the beam, and includes the machine output in MU and if a MLC is used the MLC leaf positions. For SMLC technology each segment is defined by a pair of control points having identical leaf positions and jaw positions. The first control point defines the cumulative radiation when the beam is turned on, and the second control point defines the cumulative radiation when the beam is turned off. The difference between the beam off and the beam on control points, together with the constant leaf and jaw positions, determines the amount of radiation delivered in the segment and its shape. In other technologies, such as sliding window (DMLC) or VMAT, the beam is constantly on and the leaves are constantly moved. For these technologies, each control point indicates the amount of radiation delivered, in terms of monitor units (MU), while the leaves move to the next position. It should be understood that when any of the terms control point, or segment is used in this document, it should not be taken to indicate a particular technology. Instead it should be interpreted to mean the combination of MLC opening and amount of energy delivered associated with a control point or a segment depending on the technology used.

Changing the leaf positions takes time, so it is desirable to reduce the number of segments to save time. However, reducing the number of segments will reduce the possibility to modulate the dose, which is not desirable.

Also, there is a desire to minimize the radiation, in terms of number of monitor units (MU), required to deliver the plan. The monitor units is a measure on how much energy is needed to deliver the dose.

The delivery time of a beam depends on a number of factors, such as the dose rate used for each control point, the MU per control point, the magnitude of the leaf movement between two control points. It is possible to calculate an estimation of the delivery time from the beam settings of a treatment plan. There is a desire to shorten the delivery time for several reasons, such as organ motion and patient discomfort.

It is also desirable to reduce the jaggedness of the segments. Jagged segments with for example single leaves reaching far into the MLC opening, increase the uncertainties in the dose computation. The presence of single leaves in the field increases the effects on the dose distribution from small errors in the patient positioning or in the beam modelling. For this reason there is a desire to reduce the jaggedness of the MLC openings.

Prior art attempts to achieve these goals include introducing constraints or objective functions on such parameters as the minimum segment area, maximum jaggedness, the maximum number of monitor units (MU) or the maximum delivery time. These methods require that acceptable parameter values or weights are specified before the treatment plan optimization, at a point when it cannot be known what effect these constraints or objectives will have on the dose distribution.

U.S. Pat. No. 8,961,382 aims at reducing the MU of an initial plan by producing less complex segments. This is achieved in the fluence based plans by using the fluence profiles or MLC openings from a plan as initial data to a second step, by either creating smoother fluence maps that after conversion to deliverable plan will generate less complex segments. Alternatively, it may be done in the deliverable plan by reducing the leaf movement of the leaves that travel the most. As mentioned by the authors both their techniques may compromise the plan quality in terms of the dose distribution. They suggest that the dose objective value can be computed for both the input plan and the new plan to determine if the plan quality in terms of dose is good enough.

SUMMARY OF THE INVENTION

It is an object of the invention to enable a reduction of the plan complexity of a treatment plan without loss in plan quality.

The invention relates to a method of optimizing a radiotherapy treatment plan comprising the steps of Obtaining a deliverable input treatment plan, Optimizing the deliverable input treatment plan to obtain an optimized treatment plan, using an objective function and at least one constraint, wherein the objective function is related to reducing the plan complexity in terms of at least one of the following:

minimizing the machine output, minimizing the time required to deliver the plan, maximizing the segment area, minimizing jaggedness of the MLC shapes, Whereby the at least one constraint is based on the dose distribution of the input plan and related to maintaining an acceptable dose distribution.

In the context of the invention, reducing the plan complexity involves reducing the total machine output in terms of monitor units (MU) and/or reducing the delivery time of the plan and/or increasing the area of the MLC openings (the segment area) and/or reducing the jaggedness of the MLC openings and/or reducing the number of control points/segments of the plan. This is achieved according to the invention by optimizing the treatment plan with respect to any of these parameters while applying one or more constraints related to maintaining the dose distribution. The invention enables a reduction in plan complexity without loss in plan quality, meaning that the plan complexity may be reduced while maintaining an acceptable dose distribution.

An acceptable dose distribution is one in which maximum and minimum dose targets for target areas, such as a tumour, and healthy tissue or organs at risk, respectively, are met within certain tolerances.

The invention utilizes the fact that there are many possible deliverable plans that may result in a particular dose distribution. These possible deliverable plans will have different properties with respect to plan complexity in terms of machine output (MU), delivery time, segment size, jaggedness and number of segments and the optimization makes it possible to identify and select one of the possible deliverable plans that, in addition to providing the desired dose distribution, is also advantageous from the point of view of plan complexity.

In a preferred embodiment the method involves minimizing the dose to at least one organ at risk or to healthy tissue more than what was achieved in the input plan.

The objective function may typically be related to reducing the machine output required to fulfil the plan, by minimizing one or more of the following:

The total machine output, expressed as a number of monitor units, of the plan

The machine output, expressed as a number of monitor units or weights, of one or more beams the machine output, expressed as a number of monitor units or weights, of one or more control points/segments within the beams The objective function may in other embodiments be related to reducing the delivery time of the plan by minimizing one or more of the following:

the total delivery time of the plan the delivery time of one or more beams the delivery time of one or more control points/segments within the beams In yet another embodiment, the objective function is related to the setting of the MLC leaves by one or more of the following:

Maximizing the segment area of one, some, or all control points within the plan

Minimizing the jaggedness of one, some, or all control points within the plan

According to the above, the criteria of the objective function may be related to the machine output, the delivery time or the shape or size of the segment area. The objective function may also relate to a combination of two or more of these parameters.

A method according to any one of the preceding claims, wherein the at least one constraint is based on one or more of the following:

constraining the shape of the entire or a part of one or more target DVH curves to the corresponding shapes of the DVH curves in the input plan;

constraining the shape of the entire or a part of one or more healthy tissue DVH curves to not exceed the corresponding shapes of the DVH curves in the input plan;

constraining one or more DVH points in a target DVH in dependence of the input plan;

constraining the dose in some or all voxels within a structure or the entire patient, so that the dose within a target voxel is maintained and the dose in a healthy tissue voxel is not increased compared to the dose in the input plan;

constraining some statistical measure of the dose distribution, such as mean dose or relative standard deviation of the dose distribution, within a structure in dependence of the input plan;

constraining biological indices such as EUD, gEUD, TCP, NTCP, P+ so that the same biological indices are maintained, or not decreased, for target structures and not increased for healthy tissue structures compared to the input plan;

constraining homogeneity index and/or uniformity index so that they are not increased compared to the input plan.

Using one or more of these constraints ensures that the plan will not be changed in such a way that the target receives too little radiation, or that healthy tissue receives more radiation than what is acceptable, when reoptimizing.

According to preferred embodiments the method further comprises the steps of identifying and discarding any segments and/or beams that make an insignificant contribution to the dose distribution. This will contribute to reducing the plan complexity by reducing the number of segments used. After discarding any such insignificant or tiny segments the plan is preferably reoptimized to compensate for any discarded segments or beams.

As is common in the art, the inventive method is implemented as a computer program product comprising computer readable code means which, when run in a computer will cause the computer to perform the method according to any one of the preceding claims. The computer program product is typically stored on a carrier.

The invention also relates to a computer system for performing dose calculations for radiotherapy, the system comprising processing means, said computer system having a program memory having stored therein a computer program product as defined above, in such a way that the computer program product, when executed, will control the processing means to perform the method according to an embodiment of the invention.

The computer system typically further comprises a data memory arranged to hold data to be used by the processing means when performing the optimization method, such as image data related to the patient, an initial treatment plan and/or information related to at least one scenario.

BRIEF DESCRIPTION OF THE DRAWINGS

The invention will be disclosed in more detail in the following, with reference to the appended drawings, in which FIGS. 1a, 1b and 1c illustrate a simplified example where a fluence profile may be realized by two alternative beam settings, both using three segments, FIGS. 2a and 2b illustrate the same fluence profile as in FIG. 1 but realized using two segments instead of three, FIG. 3 is a flow chart showing a first embodiment of the inventive method, FIG. 4 is a flow chart showing a second embodiment of the inventive method.

DETAILED DESCRIPTION OF PREFERRED EMBODIMENTS

Figure 5:
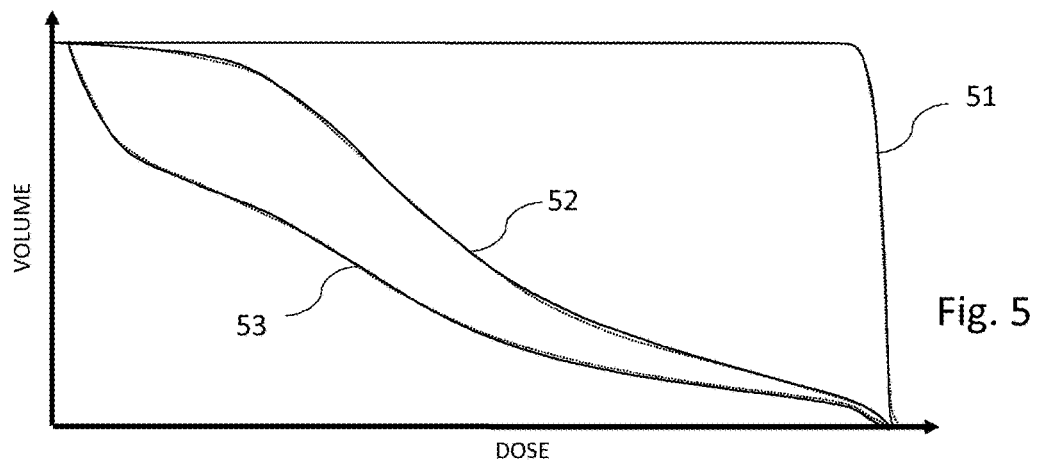
FIG. 5 is a DVH diagram illustrating the inventive method.

FIG. 1a illustrates a simplified one dimensional fluence profile required to get a certain dose in the patient. It contains five bixels, b1-b5, where b1 and b5 has half the weight as b2-b3. This fluence profile can be realized by different sets of segments (or control points), defined by different MLC openings and different machine output in MU. FIG. 1b illustrates three segment shapes s1a, s1b and s1c that together would give the desired fluence using 40 MU in total. The radiation is blocked by the solid MLC leaves, and let through the dashed openings. Segment s1a delivers 10 MU to bixel b1, segment s1b delivers 20 MU to bixels b2-b4 and segment s1c delivers 10 MU to bixel b5. FIG. 1c illustrates another beam setup containing three segments s1b, s1c, s1d that would give the same fluence profile using 30 MU in total. Segment s2a delivers 10 MU to bixel b1-b3, segment s2b delivers 10 MU to bixels b4-b5 and segment s3b adds another 10 MU to bixel b2-b4. This illustrates that there are several beam setups using the same number of beams but different machine output in MU, that will give the same fluence and thereby the same dose to the patient.

The different beam setups in a two dimensional case will have different complexity in terms of MU, delivery time, jaggedness and segment area. In this example the treatment technique is SMLC, but similar results would hold for other treatment techniques such as dynamic treatments where the beam is constantly on between the different control points of the beam. The skilled person is familiar with the concepts of fluence profiles, segments and control points.

FIG. 2a illustrates the same fluence profile as in FIG. 1a. FIG. 2b illustrates a beam setup containing two segments s1c, s2c delivered using 20 MU that give the same fluence profile as the examples in FIG. 1b and FIG. 1c. Segment s1c delivers 10 MU to bixels b1-b5 and segment s2c adds another 10 MU to bixels b2-b3. It is possible to create the same fluence profile using different numbers of segments.

As will be understood, treatment plans are normally handled in 3 dimensions. The examples here are in 2D as a simplification.

FIG. 3 is a flow chart of a method according to the invention. In step S31 an input treatment plan is obtained. This may involve determining the input treatment plan or receiving it from another unit. The skilled person knows how to obtain a treatment plan. The input treatment plan comprises a treatment setup including beam directions and control points, and a dose distribution. In step S32 an objective function is determined, which is related to minimizing the complexity of the treatment. Different types of objective functions that are relevant in this context will be discussed below. In step S33 one or more constraints based on the dose distribution of the initial plan are manually selected or automatically added. Typically the constraints relate to which changes to the delivered dose in different areas of the patient may be acceptable, including the case where no change is allowed. It will be realized that the order of steps S32 and S33 may be reversed. Also the objective and/or the constraints may be predefined.

In step S34 an optimization of the input plan is performed based on the objective and the constraints defined in steps S32 and S33. As is common in the art this is performed as an iterative process including the following substeps:

a) making a change to the plan in order to improve the dose distribution
b) evaluating the dose distribution resulting from the changed plan
c) deciding based on this evaluation to continue the optimization by repeating substeps a) and b), or to end the optimization.

Which changes to make in substep a) may be determined according to any suitable optimization method. Gradient based optimization methods have been found to work particularly well, but other methods may also be used.

The objective function determined in step S32 typically includes one or more of the following:

Minimize total machine output of the plan, defined as the number of monitor units;
Minimize the total machine output of one or more beams, defined as monitor units or beam weights;
Minimize the machine output of one or more control points/segments within the beams, defined as monitor units or segment weights;
Minimize the total delivery time of the plan;
Minimize the total delivery time of one or more beams;
Minimize the total delivery time of one or more control points/segments within the beams;
Maximize the segment area of one, some, or all control points within the plan;
Minimize the jaggedness of one, some, or all control points within the plan;

Constraints are preferably hard constraints, in the sense that they will be fulfilled at the end of the optimization. This will ensure that the dose to one or more targets and/or organs may only change in the desired direction, or that any undesired change will be within acceptable limits. Highly weighted objective functions could be used instead of hard constraints. The constraints determined in step S33 may be one or more of the following:

constraining the shape of the entire or a part of one or more target DVH curves to the corresponding shapes of the DVH curves in the input plan,
constraining the shape of the entire or a part of one or more healthy tissue DVH curves to not exceed the corresponding shapes of the DVH curves in the input plan,
constraining one or more DVH points in a target DVH in dependence of the input plan. This could mean to constrain in such a way that the same relative volume receives at least the same dose and/or at most the same dose and/or exactly the same dose as in the input plan depending on type of structure,
constraining the dose in some or all voxels within a structure or the entire patient, so that the dose within a target voxel is maintained and the dose in a healthy tissue voxel is not increased compared to the dose in the input plan,
constraining some statistical measure of the dose distribution, such as mean dose or relative standard deviation of the dose distribution, within a structure in dependence of the input plan. This could mean constraining in such a way that the statistical measure is maintained, not increased or not decreased depending on type of structure, compared to the input plan, constraining biological indices such as EUD, gEUD, TCP, NTCP, P+ so that the same biological indices are maintained or not decreased for target structures and not increased for healthy tissue structures compared to the input plan, constraining homogeneity index and/or uniformity index so that they are not increased compared to the input plan.

FIG. 4 illustrates a possible process for second embodiment of the inventive method, in which small segments are removed to reduce the total number of segments. In FIG. 4 the first three steps S41-S43 are identical to the steps S31-S33 in FIG. 3. In step 44 an optimization is started including the iteration step S45 where a change is made in the treatment plan to achieve an improvement of the objective function is performed, and the decision step S46 to see if the optimization should terminate due to optimality or some other criteria.

In FIG. 4 the procedure continues after the optimization steps S44 and S45, to include detecting and removing of very small segments, i.e. segments with low MU and/or small segment area (MLC opening) that will make an insignificant contribution to the dose distribution. These insignificant segments contribute little to the dose distribution and can therefore be removed, and are compensated by the remaining segments in the following iterations of the optimization. Entire beams that do not contribute much to the dose distribution can also be removed by the optimizer. The optimizer checks if the optimization should be terminated in step S46. The optimization may be terminated if the resulting treatment plan fulfils the objectives. The check in step S46 preferably includes determining whether or not to search for insignificant segments. Insignificant segments are tiny segments, that is, segments that are so small that their removal would only cause very small changes to the plan. If insignificant segments should not be considered, the optimization is finished in step S49, otherwise it is checked in step S47 if there are any tiny segments. If there are tiny segments they are removed in step S48, before continuing the optimization at step 45, otherwise the optimization is continuing without removing segments at step S45. The procedure continues until the optimizer determines in step S46 that no more tiny segments should be considered, at which point the optimization is finished at step S49. Preferably the optimization is continued when one or more insignificant segments are removed, but it may in some cases be assumed that the contribution of the segment is negligible and that a segment can be removed without any further optimization.

As will be understood the removal of insignificant segments may be performed at any stage of the procedure. This means, for example, that steps S47 and S48 could also be performed before step S45. However, after removing such insignificant segments it is preferable to perform a subsequent optimization to compensate for the effects of removing the segments.

FIG. 5 is a dose volume histogram (DVH) related to an input plan and the same plan after optimization according to the invention. The input plan in this case was optimized using traditional objective functions. This plan would be delivered using 400 MU. The optimization of the input plan was made using the control points from the input plan as an initial guess. The objective was to minimize the MU and the DVH curves of the initial plan were used as constraints. This means that the dose to the target should not be reduced and the dose to each organ at risk should not be increased. The diagram of FIG. 5 shows the dose in Gy along the x-axis and the portion of the volume of the relevant organ in % along the y axis. For each of the organs considered, there is a solid line and a dotted line, which more or less overlap. The dotted line relates to the dose resulting from the input plan and the solid line relates to the dose of the optimized plan. The uppermost pair 51 of dashed and solid lines relates to the target and the two pairs 52, 53 below it relate to different organs at risk. As can be seen the DVH is maintained in the target. In each of the organs at risk, the dose distribution is virtually the same, or in some points slightly reduced. This plan uses 376 MU, which is a reduction compared to the initial 400 MU. As can be seen, this reduction is achieved while maintaining the quality of the treatment plan.

Figure 6:
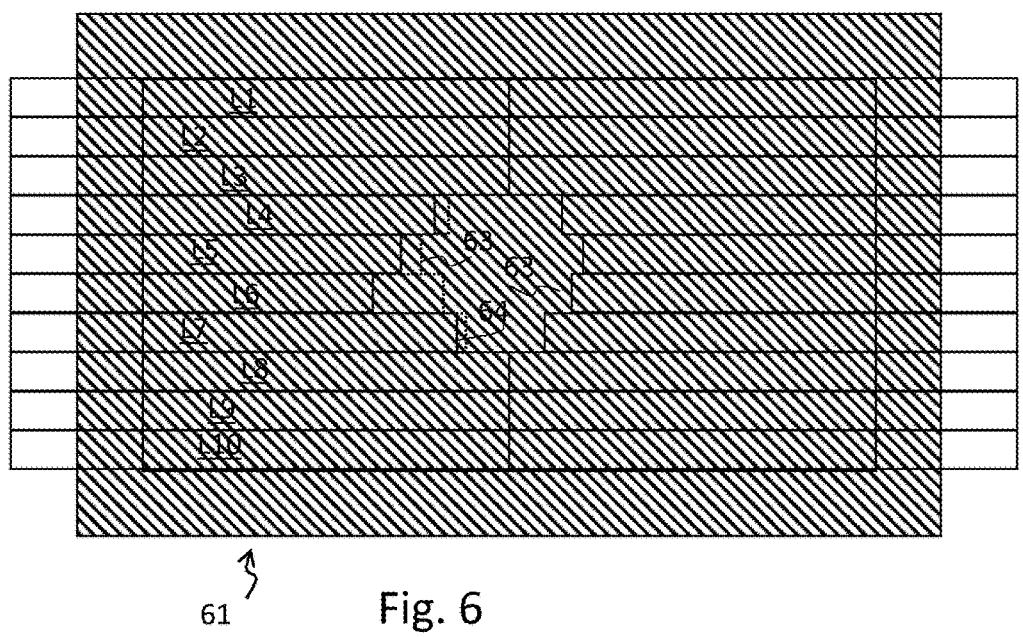
FIG. 6 illustrates changes in MLC settings between an input plan and an optimized plan, respectively.

FIG. 6 illustrates by way of example the changes in MLC settings in an input treatment plan before and after optimization. The optimization has been performed with the objective function to reduce the machine output in MU. A simplified MLC 61 is shown having 10 leaf pairs numbered L1-L10. Reducing MU is compensated by using larger MLC openings, as can be seen for leaf pairs number 4, 5, 6 and 7. For each of them, dashed lines represent the end points as defined in the input treatment plan, and solid lines represent the end points according to the optimized plan. As can be seen in FIG. 6, leaf pairs 4-7 have moved compared to the input treatment plan, to enlarge the MLC segment.

In addition to the optimization discussed above, the optimizer can also be instructed to remove segments that do not contribute much to the dose e.g. segments with small MLC openings, and/or segments with low energy. Entire beams that do not contribute much to the dose distribution can also be removed by the optimizer. The removal of control points and beams can be performed before the optimization is started or at any iteration during the plan optimization.

A penalty on dose to reduce dose to healthy tissue outside the tumour or within certain structures can be included in the objective function.

Figure 7:
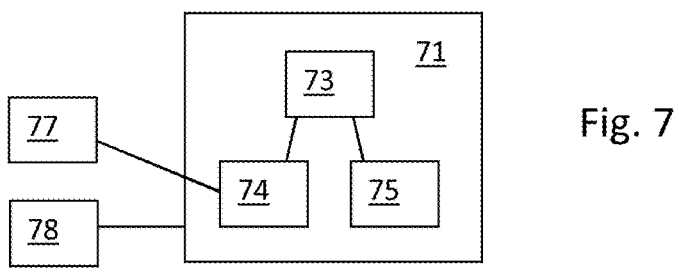
FIG. 7 shows, schematically, a computer system in which the inventive method may be implemented.

FIG. 7 is a schematic representation of a computer system in which the inventive method may be performed. A computer 71 comprises a processor 73, a data memory 74 and a program memory 75. The data memory 74 is arranged to receive from a CT imager 77 a set of CT scans of the relevant area of the patient taken over time to form a 4DCT scan. The CT scans are not necessarily received directly from the CT imager 77; they may alternatively be received from some other unit by any known communication method. Preferably, a user input means 78 is also present, in the form of a keyboard, a mouse, a joystick, voice recognition means or any other available user input means.

A treatment plan is stored in the data memory 74. The treatment plan may be generated in the computer 71, or received from another storage means in any way known in the art.

The data memory 74 may also hold one or more different objective functions and/or constraints to be used in the optimization. Alternatively, the objective function and/or constraints to be used in an optimization procedure may be entered by means of the user input means 78 or other input means, or generated in the computer 71. As will be understood, the data memory 74 is only shown schematically. There may be several data memory units, each holding one or more different types of data, for example, one data memory for the objective function, one for the constraints, etc.

The program memory 75 holds a computer program arranged to control the processor to perform the optimization as defined in FIG. 3 or FIG. 4. It will be understood that not all of the steps of the method of FIG. 3 or 4 are necessarily performed in the computer 71.

The invention claimed is:

1. A method of optimizing a radiotherapy treatment plan for a radiotherapy treatment machine, the method comprising the steps of:
    (a) obtaining an existing deliverable input treatment plan; and
    (b) modifying, by a processor, the existing deliverable input treatment plan to reduce plan complexity of the input treatment plan to obtain an optimized treatment plan by using an objective function and at least one constraint, wherein the input treatment plan is configured to determine a treatment setup to be implemented by the radiotherapy treatment machine, the treatment setup comprising a dose distribution and at least one of:
        (1) a machine output for the radiotherapy treatment machine;
        (2) a delivery time required by the radiotherapy treatment machine to deliver the plan;
        (3) a segment area of the radiotherapy treatment machine; or
        (4) a jaggedness of multi-leaf collimator (MLC) shapes for the radiotherapy treatment machine,
    wherein the objective function is related to reducing the plan complexity in terms of at least one of the following:
        (i) minimizing the machine output of the treatment setup;
        (ii) minimizing the delivery time of the treatment setup;
        (iii) maximizing the segment area of the treatment setup; or
        (iv) minimizing the jaggedness of multi-leaf collimator (MLC) shapes of the treatment setup,
    (c) whereby the at least one constraint is based on the dose distribution of the input treatment plan and related to maintaining an acceptable dose distribution for the radiotherapy treatment machine, the treatment setup being implemented by the radiotherapy treatment machine.

2. The method according to claim 1, further comprising minimizing the dose to at least one organ at risk or to healthy tissue more than what was achieved in the input plan.

3. The method according to claim 1, wherein the objective function is related to reducing the machine output required to fulfil the optimized plan, by minimizing one or more of the following:
    (a) the total machine output, expressed as a number of monitor units, of the optimized plan;
    (b) the machine output, expressed as a number of monitor units or weights, of one or more beams; or
    (c) the machine output, expressed as a number of monitor units or weights, of one or more control points/segments within the beams.

4. The method according to claim 1, wherein the objective function is related to reducing the delivery time of the optimized plan by minimizing one or more of the following:
    (a) the total delivery time of the optimized plan;
    (b) the delivery time of one or more beams; or
    (c) the delivery time of one or more control points/segments within the beams.

5. The method according to claim 1, wherein the objective function is related to the setting of the MLC leaves by one or more of the following:
    (a) maximizing the segment area of one, some, or all control points within the optimized plan; or
    (b) minimizing the jaggedness of one, some, or all control points within the optimized plan.

6. The method according to claim 1, wherein the at least one constraint is based on one or more of the following:
    constraining the shape of the entire or a part of one or more target dose volume histogram (DVH) curves to the corresponding shapes of the DVH curves in the input plan;
    constraining the shape of the entire or a part of one or more healthy tissue DVH curves to not exceed the corresponding shapes of the DVH curves in the input plan;
    constraining one or more DVH points in a target DVH in dependence of the input plan;
    constraining the dose in some or all voxels within a structure or the entire patient, so that the dose within a target voxel is maintained and the dose in a healthy tissue voxel is not increased compared to the dose in the input plan;
    constraining a statistical measure of the dose distribution within a structure in dependence of the input plan;
    constraining a biological index so that the same biological index is maintained, or not decreased, for target structures and not increased for healthy tissue structures compared to the input plan; or
    constraining homogeneity index or uniformity index so that they are not increased compared to the input plan.

7. The method according to claim 1, further comprising the steps of identifying and discarding any segments or beams that make an insignificant contribution to the dose distribution.

8. The method according to claim 7, further comprising the step of reoptimizing the optimized plan to compensate for any discarded segments or beams.

9. A computer program product comprising a non-transitory computer readable medium storing computer readable code which, when run in the processor of a computer will cause the computer to perform the method according to claim 1.

10. The computer program product of claim 9, stored on a carrier.

11. A computer system for performing dose calculations for radiotherapy, the system comprising processing means, said computer system having a program memory having stored therein the computer program product according to claim 9 in such a way that the computer program product, when executed, will control the processing means.

12. The computer system according to claim 11, further comprising a data memory arranged to hold data to be used by the processing means when performing the optimization method, said data comprising at least one of image data related to the patient, the input treatment plan, or information related to at least one scenario.

13. The method according to claim 6, wherein the statistical measure of the dose distribution is at least one of a mean dose or a relative standard deviation of the dose distribution.

14. The method according to claim 6, wherein the biological index is at least one of EUD, gEUD, TCP, NTCP, or P+.

* * * * *